United States Patent [19]
Williams et al.

[11] Patent Number: 5,468,520
[45] Date of Patent: Nov. 21, 1995

[54] PROCESS FOR BARRIER COATING OF PLASTIC OBJECTS

[75] Inventors: Joel L. Williams, Cary; Susan L. Burkett, Hillsborough, both of N.C.; Shel McGuire, Omaha, Nebr.

[73] Assignee: Becton, Dickinson and Company, Franklin Lakes, N.J.

[21] Appl. No.: 265,164

[22] Filed: Jun. 24, 1994

Related U.S. Application Data

[63] Continuation-in-part of Ser. No. 125,704, Sep. 23, 1993, Pat. No. 5,364,666.

[51] Int. Cl.$^6$ .................................................... B05D 3/06

[52] U.S. Cl. .......................... 427/560; 427/296; 427/346; 427/348; 427/371; 427/571; 427/574; 427/575; 427/579; 427/585; 427/598; 427/600

[58] Field of Search ................................... 427/536, 539, 427/547, 553, 560, 571, 574, 575, 579, 598, 600, 419.3, 296, 346, 348, 371

Primary Examiner—Bernard Pianalto
Attorney, Agent, or Firm—Nanette S. Thomas

[57] ABSTRACT

A method for sequentially depositing a silicon oxide based film as a barrier on a substrate. The film is useful for providing an effective barrier against gas permeability in containers and for extending shelf-life of containers, especially plastic evacuated blood collection devices.

9 Claims, 5 Drawing Sheets

PROCESS FOR BARRIER COATING OF PLASTIC OBJECTS

This application is a continuation-in-part of U.S. Ser. No. 08/125,704, filed on Sep. 23, 1993, now U.S. Pat. No. 5,364,666.

BACKGROUND OF THE INVENTION

1. Field of the Invention

This invention relates to a method for depositing a barrier coating to plastic containers for improving the effective barrier of the plastic container against gas and water permeability.

2. Description of the Related Art

In numerous fields of technology, it is necessary to apply very thin coatings of pure substances to certain objects. An example is window glass which is provided with a thin coating of metal oxide in order to filter certain wavelength ranges out of sunlight. In semi-conductor technology, thin coatings of one or more substances are often applied to a substrate. It is especially important that the thin coatings not only be pure, but also that they be precisely measured out so that the coating thickness and, in the case of coatings of chemical compounds, their composition will be accurately repeatable. These coating thicknesses are, as a rule, between two and several thousands of nanometers.

A variety of methods are known for applying thin coatings to films, glass and other substrates. Such processes for depositing $SiO_x$ onto plastic objects are disclosed in U.S. Pat. No. 5,053,244 and European Patent No. 0 299 754. Most specifically, these processes can provide excellent barrier properties to plastic films which have not been exposed to dust. However, these processes provide only minor barrier properties to three-dimensional plastic objects or films that are exposed to dust.

It is believed that the inability to obtain a good barrier on three-dimensional plastic objects is due to the lack of cleanliness of the object's surface since most three dimension objects are exposed to dust during fabrication.

In the process of depositing $SiO_x$ on thin films, the $SiO_x$ barrier coating is applied under vacuum conditions to a clean film. Typically, film is extruded under very clean conditions and immediately wound into a large roll. As a consequence, the film surfaces, with the exception of the outside layer, are never exposed to particles in air such as dust.

It is believed that the reason for the lack or minimum improvement in permeability of three-dimensional objects coated with $SiO_x$ is that the surface of the three-dimensional object has a contaminated surface. It is further believed that the contamination is due to foreign surface particles that settle on the object due to its exposure to air.

Even though $SiO_x$ is evenly deposited on the surface of an object at about 500 to 1000 Å in thickness, because foreign surface particles, that are on the order of 5000 to 50000 Å in diameter, and may be on the surface of the object, portions of the surface are not coated with the $SiO_x$ because of the shielding effect caused by the foreign surface particles.

Therefore, a need exists to remove and/or redistribute contamination from the surface of objects that are to be coated with $SiO_x$ to improve the process for applying $SiO_x$ to the objects and more particularly, to improve the barrier properties of the objects.

SUMMARY OF THE INVENTION

The present invention is a process for sequentially depositing a barrier composition over the outer surface of an article, such as a composite container.

Preferably, the barrier composition is a silicon oxide based film. Such film desirably is derived from volatile organosilicon compounds or gases.

Most preferably, the method for sequentially depositing a silicon oxide based film on an article, such as a plastic collection tube comprises the following steps:

(a) controllably flowing a gas stream including an organosilicon compound into a plasma;

(b) depositing a first silicon oxide based film onto the surface of the article while maintaining a pressure of less than about 100 microns Hg during the depositing;

(c) removing and/or redistributing foreign surface particles from the surface of the article; and (d) depositing a second silicon oxide based film onto the surface of the article over the first silicon based film by repeating steps (a) through (b) above.

The organosilicon compound is preferably combined with oxygen and helium and at least a portion of the plasma is preferably magnetically confined adjacent to the article during the depositing, most preferably by an unbalanced magnetron.

Preferably, the foreign surface particles are removed and/or redistributed from the surface of the article by ultrasonic vibrations or wiping. Most preferably the foreign surface particles are removed and/or redistributed with pressurized gas.

Alternatively, the present invention relates to a process for producing a plasma and treating substrates with the plasma by means of microwaves in a chamber having metal walls. The microwaves are repeatedly reflected at the metal walls so that the chamber has numerous microwave modes. By means of permanent magnets, which are placed either inside or outside the chamber in the vicinity of the substrate that is to be coated, an electron-cyclotron resonance is produced which permits a locally controlled ignition of the plasma.

Most preferably, the method for sequentially depositing a silicon oxide based film on an article by means of microwaves, such as a plastic collection tube comprises the following steps:

(a) introducing a first reactive gas comprising a hydrogen silicide gas into a chamber;

(b) introducing a second reactive gas comprising at least one gas selected from the group consisting of oxygen and an oxygen containing compound into said chamber;

(c) admitting microwaves into said chamber;

(d) producing a magnetic field in said chamber wherein said magnetic field and the microwaves being sufficient to produce a region of electron cyclotron resonance in said chamber which produces a plasma of both reactive gases;

(e) exposing a substrate to said plasma of both gases in said region, thereby depositing a first $SiO_x$ coating on said article;

(f) removing and/or redistributing foreign surface particles from the surface of the article; and (g) depositing a second $SiO_x$ coating onto the surface of the article over the first $SiO_x$ coating by repeating steps (a) through (e) above.

The first reactive gas is most preferably a hydrogen silicide gas.

Preferably, the foreign surface particles are removed and/or redistributed from the surface of the article by ultrasonic vibrations or wiping. Most preferably the foreign 'surface particles are removed and/or redistributed with pressurized gas.

Preferably, the film provides a transparent, translucent or colorless appearance and may have printed matter applied thereon.

Alternatively, the process of depositing a silicon oxide based film can be accomplished by evaporating or sputtering a metal or metal oxide instead of plasma.

The advantage achieved by the process of sequentially depositing a silicon oxide based film with the intermittent removal and/or redistribution of foreign surface particles from the surface of the article is that improved permeability is observed.

A further advantage is that the process of the present invention improves the permeability of three-dimensional objects that has not been achieved with conventional deposition processes typically used with thin films.

A significant advantage of the process of the present invention is that the intermittent step of removing and/or redistributing foreign surface particles on the surface of the article exposes the regions shielded by the foreign surface particles for the depositing of a second $SiO_x$ coating. Therefore, a significant reduction in permeability of the article is due to the complete $SiO_x$ surface coverage that is obtained by the sequential deposition technique and intermittent step of removing and/or redistributing the foreign surface particles.

DETAILED DESCRIPTION

Figure 1:
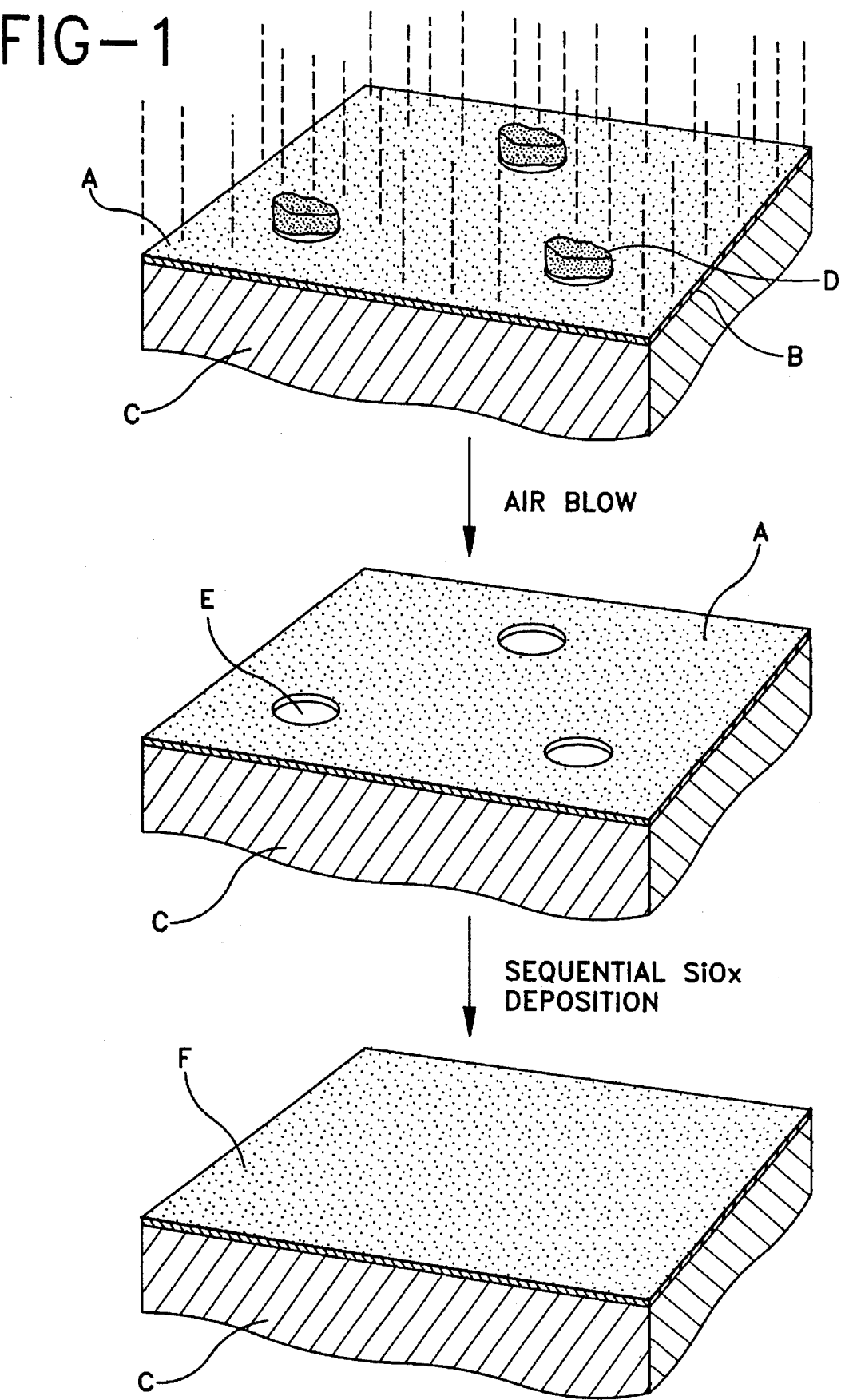
FIG. 1 is a general schematic diagram illustrating the sequential depositing of $SiO_x$.

The present invention may be embodied in other specific forms and is not limited to any specific embodiment described in detail which is merely exemplary. Various other modifications will be apparent to and readily made by those skilled in the art without departing from the scope and spirit of the invention. The scope of the invention will be measured by the appended claims and their equivalents.

The method for sequentially depositing a silicon oxide based film on a substrate is preferably conducted in a previously evacuated chamber of glow discharge from a gas stream. The gas stream preferably comprises at least three components: a volatilized organosilicon component, an oxidizer component such as oxygen and an inert gas component.

Suitable organosilicon compounds for the gas stream are liquid at about ambient temperature and when volatilized have a boiling point above about ambient temperature and include methylsilane, dimethysilane, trimethylsilane, diethylsilane, propylsilane, phenylsflane, hexamethyldisilane, 1,1,2,2-tetramethyl disilane, bis (trimethylsilane) methane, bis (dimethylsilyl) methane, hexamethyldisiloxane, vinyl trimethoxy silane, vinyl triethyoxy silane, ethylmethoxy silane, ethyltri methoxy silane, divinyltetramethyldisiloxane, divinylhexamethyltrisiloxane, and trivinylpentamethyltrisiloxazane.

Among the preferred organosilicons are 1,1,3,3-tetramethyldisiloxane, hexamethyldisiloxane, vinyltrimethylsilane, methyltrimethoxysilane, vinyltrimethoxysilane and hexamethyldisilazane. These preferred organosilicon compounds have boiling points of 71° C., 101° C., 55.5° C., 102° C., 123° C. and 127° C. respectively.

The inert gas of the gas stream preferably is helium or argon. Most preferably the inert gas is helium.

The volatilized organosilicon component is preferably admixed with the oxygen component and the inert gas component before being flowed into the chamber. The quantities of these gases being so admixed are controlled by flow controllers so as to adjustably control the flow rate ratio of the gas stream components.

The organosilicon compound and oxygen of the gas stream during the depositing are preferably in a flow rate ratio between about 1.2:1 to about 1:1.8. When the inert gas is helium or argon, then the preferred flow rate ratio of organosilicon compound, oxygen and inert gas is about 1 to 1.8:1.5 to 1.8 to 2.3.

In addition to the necessary organosilicon, oxygen and inert gas in the gas stream, minor amounts (not greater than about 1:1 with respect to the organosilicon, more preferably about 0.4 to 1.1:1 with respect to the organosilicon) of one or more additional compounds in gaseous form may be included for particular desired properties. These additional compounds include, but are not limited to a lower hydrocarbon such as propylene, methane or acetylene, or nitrogen. In particular, nitrogen increases the deposition rate, improves the transmission and reflection optical properties on glass, and varies the index of refraction in response to varied amounts of $N_2$. The addition of nitrous oxide to the gas stream increases the deposition rate and improves the optical properties, but tends to decrease the film hardness.

A particularly preferred gas stream composition has 20 to 40 SCCM organosilicon, 20 to 40 SCCM $0_2$, 40 to 60 SCCM He, 1 to 10 SCCM propylene and 5 to 20 SCCM $N_2$.

A glow discharge plasma is established in the previously evacuated chamber which is derived from one or more of the gas stream components, and preferably is derived from the gas stream itself. The article is positioned in the plasma, preferably adjacent the confined plasma, and the gas stream is controllably flowed into the plasma. A first silicon oxide based film is deposited on the substrate.

As shown in FIG. 1, the first silicon oxide based film A does not completely cover surface B of substrate C. It is believed that complete coverage cannot be achieved with the first silicon oxide based film because of surface shielding caused by foreign surface particles D. In effect, no silicon oxide based film is applied beneath the particles.

Therefore, before the second silicon oxide based film is applied, the shielding particles are removed and/or redistributed from the surface of the substrate with compressed gas. The compressed gas is most preferably air, nitrogen, argon or oxygen. The pressure of the gas is preferably at about 25 psi. Shielded regions E are exposed after the foreign surface particles are removed and/or redistributed with the compressed gas.

After the foreign surface particles are removed and/or redistributed with the compressed gas, the substrate is then again subjected to the glow discharge plasma process described above to deposit a second silicon based oxide film F and to produce a substantially pin hole free barrier coating on the substrate.

The deposition method of the present invention is preferably practiced at relatively high power and quite low pressure. A pressure less than about 100 microns Hg (0.1 Torr) should be maintained during the deposition, and preferably the chamber is at a pressure between about 43 to about 49 microns Hg during the deposition of film.

The substrate is electrically isolated from the deposition system (except for electrical contact with the plasma) and is at a temperature of less than about 80° C. during the depositing. That is, the substrate is not deliberately heated.

Figure 2:
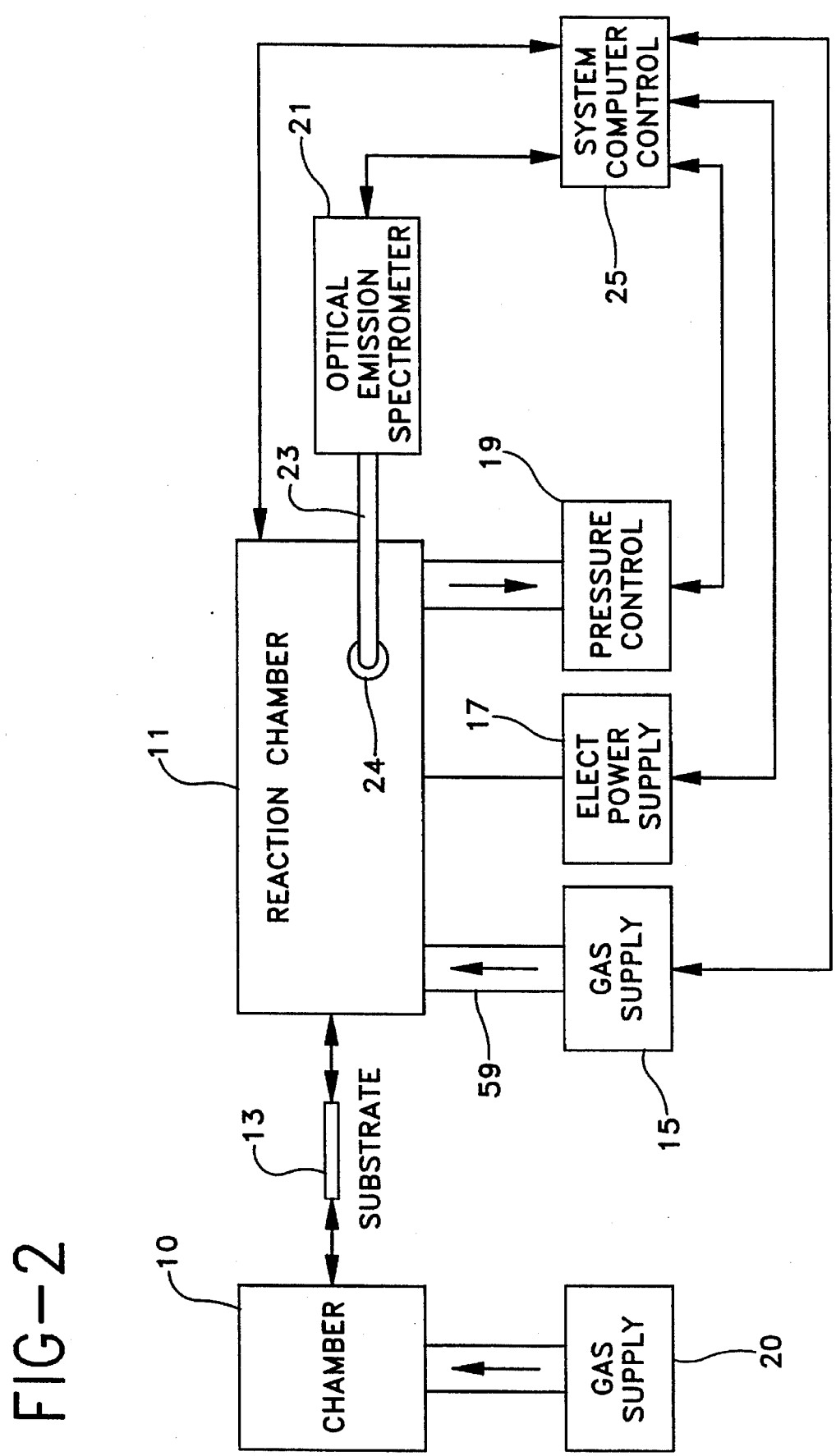
FIG. 2 is a general schematic diagram illustrating a plasma system utilizing the various aspects of the present invention.

Referring to FIG. 2, the system for sequentially depositing a silicon oxide based film and removing and/or redistributing surface particles is schematically illustrated. The system for depositing a silicon oxide based film comprises an enclosed reaction chamber 11 in which a plasma is formed and in which a substrate 13, is placed for depositing a thin film of material on it. The substrate can be any vacuum compatible material, such as plastic. One or more gases are supplied to the reaction chamber by a gas supply system 15. An electric field is created by a power supply 17, and a low pressure is maintained by a pressure control system 19. An optical emission spectrometer 21 is connected through an optical fiber light transmission medium 23 to the reaction chamber in some appropriate manner to couple the visible and near visible (especially the ultraviolet range) emission of the plasma to the spectrometer. A quartz window 24 in a side wall of the reaction chamber can be used to optically couple the plasma emission with external fiber medium 23. A general control system 25, including a computer control portion, is connected to each of the other components of the system in a manner to receive status information from and send controlling commands to them.

The reaction chamber can be of an appropriate type to perform any of the plasma-enhanced chemical vapor deposition (PECVD) or plasma polymerization process.

The system for removing and/or redistributing foreign surface particles includes an enclosed chamber 10 with a compressed gas supply system 20 for removing and/or redistributing the foreign surface particles that may be on the substrate.

Figure 3:
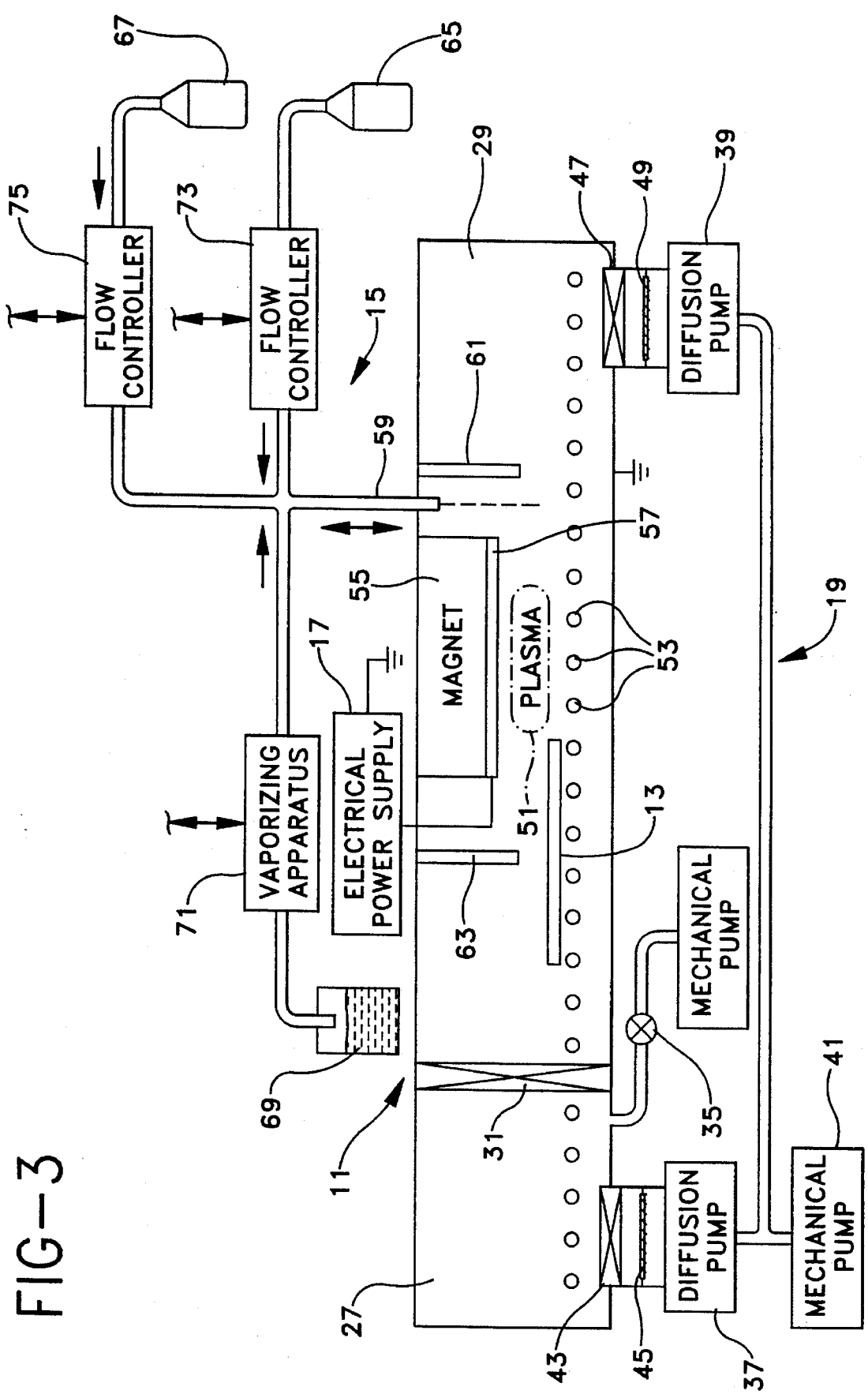
FIG. 3 is a schematic diagram illustrating a side sectional view of the plasma deposition chamber and its associated equipment as related to FIG. 2.

FIG. 3 shows a detailed side sectional schematic of the system of FIG. 2. In particular, reaction chamber 11 is divided into a load lock compartment 27 and a process compartment 29 by an isolation gate valve 31. Pressure control system 19 includes a mechanical pump 33 connected to load lock compartment 27 by a valve 35. The pressure control system also includes diffusion pumps 37 and 39, and an associated mechanical pump 41. Diffusion pump 37 is connected to load lock compartment 27 through an isolation gate valve 43 and an adjustable baffle 49. Similarly, diffusion pump 39 is connected to process compartment 29 through an isolation gate valve 47 and an adjustable baffle 49. Baffle 49 is controlled by system control 25, while a coating process is being carried out, in order to maintain the internal pressure at a desired value.

The substrate to be coated is first loaded into load lock compartment 27 with valve 31 closed. Mechanical pump 33 then reduces the pressure most of the way to the high vacuum region. Diffusion pump 37 is then operated to reduce the pressure further, to about $5 \times 10^{-6}$ Torr. The operating pressure is about 46 microns for a PECVD or plasma polymerization process and is achieved by flowing the process gases into the reaction chamber and throttling diffusion pump 39 using baffle 49. During loading and unloading operations, diffusion pump 39 maintains the deposition chamber 29 at the operating pressure. Once load lock compartment 27 is reduced to base pressure, valve 31 is opened and substrate 13 is moved into process compartment 29.

During the deposition process, substrate 13 is moved back and forth by means 53 through a plasma region 51, a number of times in order that the thin film deposited on the outer surface of the substrate has a desired uniform thickness.

A magnetron is positioned within chamber 29, formed of a magnetic structure 55 and a cathode 57. Power supply 17 has its output connected between cathode 57 and a metallic body of the reaction chamber. The magnetron creates an appropriate combination of magnetic and electrical fields in plasma region 51 in order to create a plasma there when the proper gases are introduced into the process compartment. The substrate is maintained electrically isolated and is passed directly through the plasma region.

The gaseous components necessary for the plasma to form in plasma region 51 are introduced into deposition chamber 29 by a conduit 39. Gas flows within deposition chamber 29 from diffusion pump 39. A pair of baffles 61 and 63 on either side of the magnetron help to confine the gas flow to plasma region 51.

After a first coating of the silicon oxide based film has been deposited on the substrate, the substrate is subjected to a stream of compressed gas at about 25 psi in chamber 10. Foreign surface particles on the substrate are removed and/or redistributed. The substrate is then returned to chamber 11 for a second coating of the silicon oxide based film.

Figure 4:
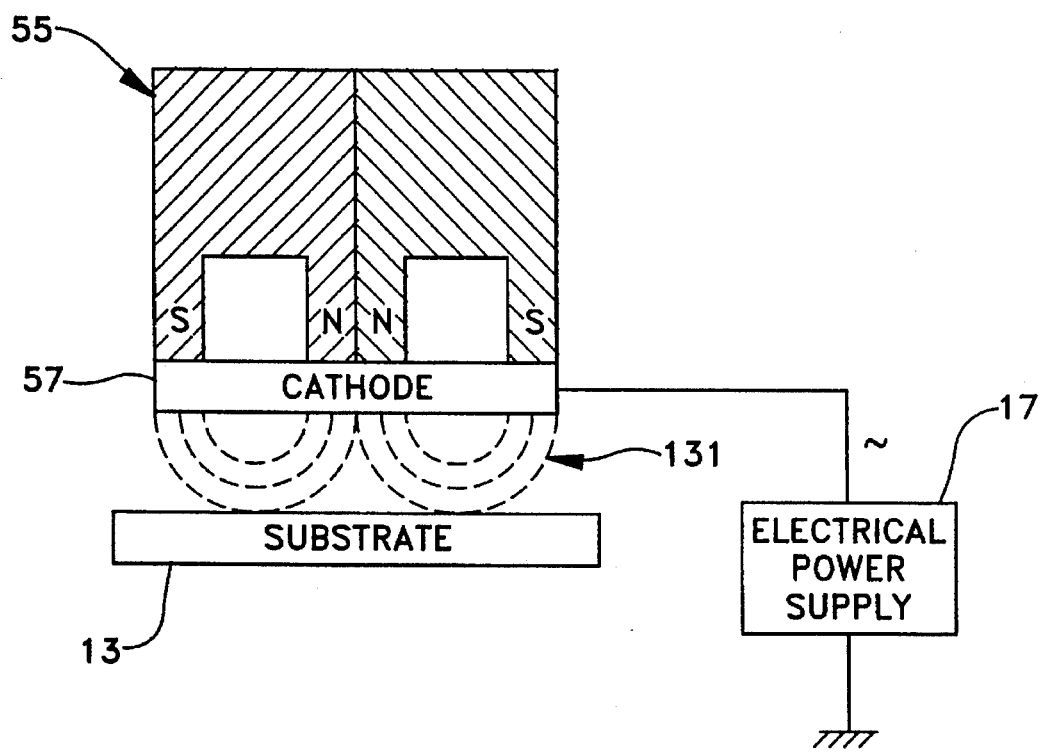
FIG. 4 illustrates the use of a balanced magnetron in the system of FIG. 3.

The magnetron used in process compartment 29 can be of a planar magnetron form as shown in FIG. 4. A cross-sectional view of the magnet structure 55 is provided at a vertical plane. In plan view, the structure of FIG. 4 is elongated in a direction normal to the plane of paper.

The structure of FIG. 4 is termed a balanced magnetron. Its magnetic lines of force 131 travel between one of the outer south magnetic poles and a central north pole. As is well known, electrons and ions travel in a spiral around a magnetic force line and along it, under influence of a combination of the magnetic field forces and the electric field forces formed by the cathode and the process chamber metal case. Cathode 57 is generally made of titanium or quartz, but sputtering is prevented from happening because of the higher pressure used in the deposition system of FIG. 3.

Figure 5:
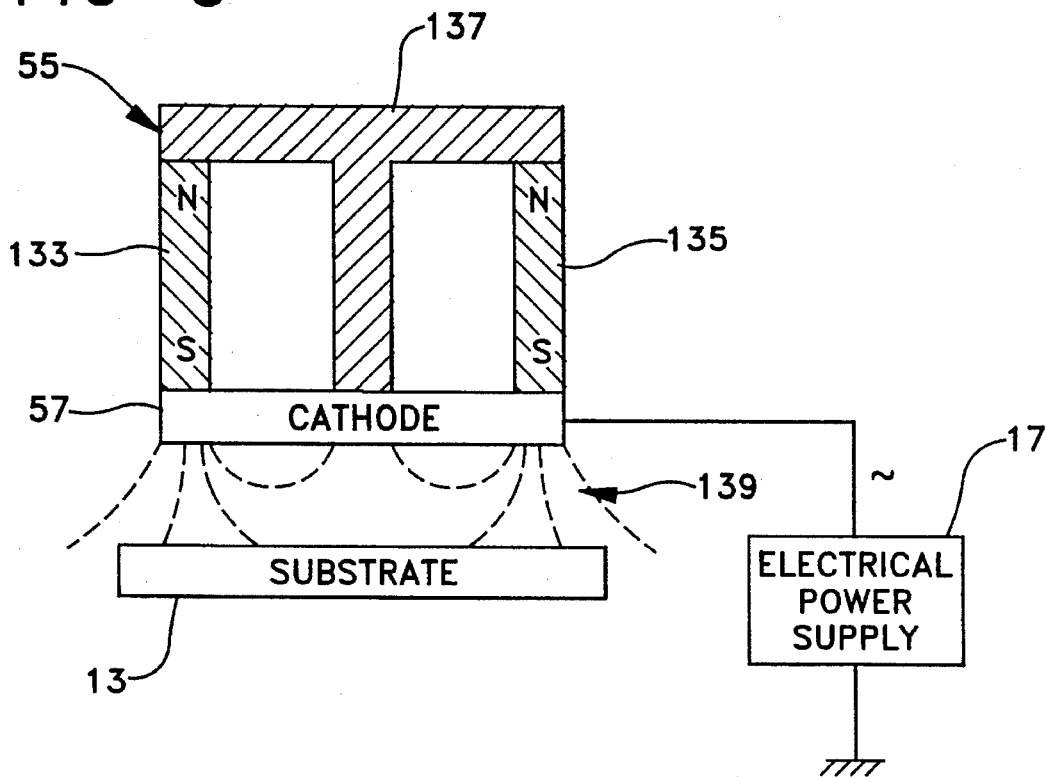
FIG. 5 illustrates the use of an unbalanced magnetron in the system of FIG. 3.

An unbalanced magnetron that alternatively can be utilized in the system of FIG. 3 is shown in FIG. 5. Outside magnets 133 and 135 are arranged with a soft iron core 137 middle. Only the south magnetic poles are positioned against a cathode 57, the north pole faces being oriented away from the cathode. The result is that a substantial proportion of the magnetic field line follow a much longer path in extending between the magnetic south and north pole regions.

The magnetron structures of FIGS. 4 and 5 are suitable for low frequency operation of power supply 17. An example frequency is 40 kHz. However, there can be some advantages from operating at a much high frequency, such as in the radio frequency range of several megahertz.

Figure 6:
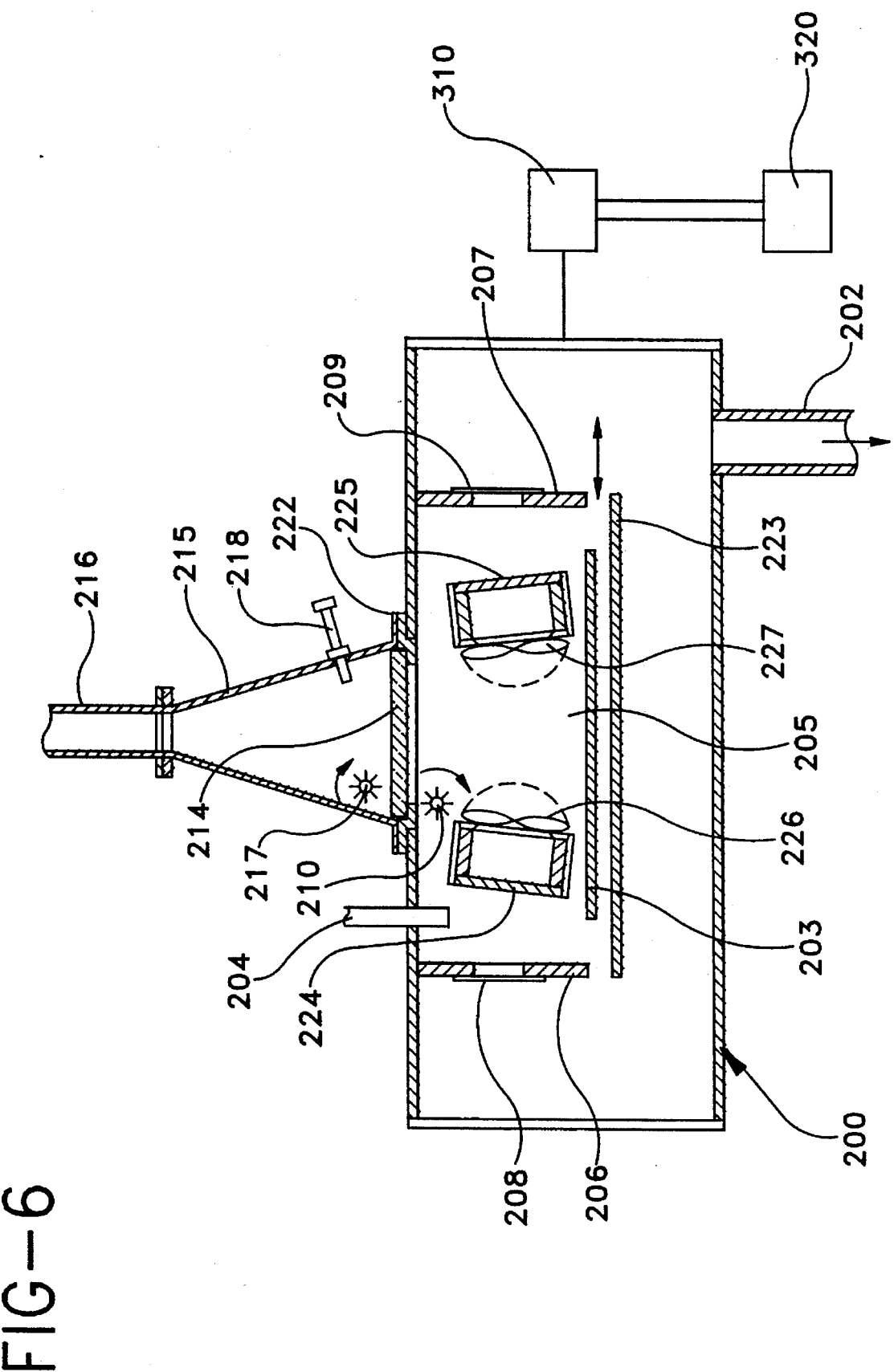
FIG. 6 is a schematic diagram illustrating a side sectional view of the chamber for producing microwaves and its associated equipment.

Referring to FIG. 6, an alternative system for depositing silicon oxide by means of microwaves is illustrated. A housing 200 is evacuated through a connection 202. Disposed in the housing is a linearly movable support 203 with a substrate that is to be coated. A plasma is produced in front of the substrate support 203, so that three-dimensional substrates can be coated. The coating is performed by means of a gas which is fed into a chamber 205 through an inlet connector 204 and the substrate is there ionized. Chamber 205 has walls 206, 207 and 223. Lateral walls 206 and 207 each have a mesh 208 and 209 which is permeable to microwaves and which assures the transparency of the chamber for a gas exchange. Also provided in chamber 205 is a rotable metal reflector 210 which is in the form of a paddle wheel. The magnet arrangement consists of two systems 224 and 225 which are arranged in symmetry with an imaginary straight line along the axis of the waveguide 216 and of the horn radiator 215. The microwaves from horn radiator 215 enter into chamber 205 through microwave window 214. Horn radiator 215 is connected to a microwave conductor 216 which in turn is connected to a microwave transmitter which is not represented. The microwave power immediately behind the microwave window 214 is made such that it does not result in spontaneous ignition of the plasma in the window area.

In horn radiator 215, which rests on a flange 222, there is disposed a rotable metal reflector 217 and rods 218 of metal or of a dielectric are disposed opposite the reflector so as to influence the field distribution.

The apparatus is operated wherein microwave power radiated in the form of a lobe by horn radiator 215 is injected into chamber 205 and repeatedly reflected on walls 206, 207 and 223 and on substrate support 203. This causes a number of standing waves with nodes and crests in different positions to form in chamber 205. The standing waves are also referred to as a multimode system. The super-imposition of many individual vibrations results in a wave field which is substantially more uniform than the lobe radiated by horn radiator 215. Additional mixture of waves or modes can be achieved by the rotating metal reflectors 210 and 217 which are wave agitators.

Two cyclotron resonance regions 226 and 227 form, which serve as ignition zones for the plasma. The magnet system produces the electron-cyclotron resonance. The gas particles ionized by the microwaves are drawn by the Lorenz force into a path curving around the magnetic lines of force. The frequency of the rotation of a charged particle in a homogeneous magnetic field is independent of its radius of curvature if the velocities are not too great, and it depends only on the specific charge.

A gaseous hydrogen silicide, i.e., Si and $H_{2n+2}$, is decomposed with the feeding in of oxygen or an oxygenous compound in a plasma discharge. The chamber is exposed to microwaves and a magnetic field of sufficient strength to form a plasma of both gases. A substrate in thus coated with $SiO_x$, wherein $x$ is determined by the ratio of gases admitted.

Additionally, a gaseous monomer from the group of the silicon hydrocarbons can be introduced into the plasma discharge.

The alternative system includes means for removing and/or redistributing foreign surface particles. This includes an enclosed chamber 310 with a compressed gas supply system 320 for removing and/or redistributing the foreign surface particles that may be on the substrate.

After a first coating of the silicon oxide based film has been deposited on the substrate, the substrate is subjected to a stream of compressed gas at about 25 psi in chamber 310. Foreign surface particles on the substrate are removed and/or redistributed. The substrate is then returned to chamber 205 for a second coating of the silicon oxide based film.

The silicon oxide based film or blends thereof used in accordance with this disclosure, may contain conventional additives and ingredients which do not adversely affect the properties of articles made therefrom.

Various other modifications will be apparent to and may be readily made by those skilled in the art without departing from the scope and spirit of the invention.

A variety of substrates can be coated with a barrier composition by the process of the present invention. Such substrates include, but are not limited to packaging, containers, bottles, jars, tubes and medical devices.

A variety of processes are also available in addition to plasma deposition for depositing a barrier composition. Such processes include, but are not limited to radio frequency discharge, direct or dual ion beam deposition, sputtering, or evaporation.

The following examples are not limited to any specific embodiment of the invention, but are only exemplary.

What is claimed is:

1. A method of sequentially depositing a silicon oxide based film on a plastic substrate in a previously evacuated chamber by glow discharge comprising:
   (a) introducing a first reactive gas comprising a hydrogen silicide into a first chamber;
   (b) introducing a second reactive gas comprising at least one gas selected from the group consisting of oxygen and an oxygen containing compound into said first chamber;
   (c) admitting microwaves into said first chamber;
   (d) producing a magnetic field in said first chamber, said magnetic field and said microwaves being sufficient to produce a region of electron cyclotron resonance in said first chamber which produces a plasma of both said reactive gases;
   (e) exposing a substrate to said plasma of both gases in said region, thereby deposition a first coating of $SiO_x$ on said substrate;
   (f) removing or redistributing foreign particles from the surface of said substrate and
   (g) repeating steps (a) through (e) above, thereby depositing a second coating of $SiO_x$ on said substrate.

2. The process of claim 1 wherein said substrate is a three-dimensional object.

3. The process of claim 2 wherein said substrate is blood collection tube.

4. The process of claim 1 wherein a gaseous monomer selected from the group of silicon hydrocarbons is introduced into the plasma discharge.

5. The method according to claim 1, wherein said foreign surface particles are removed and/or redistributed with a pressurized gas stream.

6. The method of claim 5 wherein said pressurized gas stream is nitrogen or argon at about 25 psi.

7. The method of claim 1, wherein said foreign surface particles are removed and/or redistributed with ultrasonic vibrations.

8. The method of claim 1, wherein said foreign surface particles are removed and/or redistributed by wiping said substrate.

9. The method of claim 1, wherein a gaseous monomer selected from the group of silicon hydrocarbons is introduced into the plasma discharge.

* * * * *